(12) United States Patent  
Hayashi et al.

(10) Patent No.: US 7,364,298 B2
(45) Date of Patent: Apr. 29, 2008

(54) OPHTHALMIC APPARATUS

(75) Inventors: Akihiro Hayashi, Toyokawa (JP);
Masaaki Hanebuchi, Nukata-gun (JP);
Tetsuyuki Miwa, Nukata-gun (JP);
Mikio Kurachi, Hazu-gun (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 11/589,787

(22) Filed: Oct. 31, 2006

(65) Prior Publication Data

US 2007/0097317 A1    May 3, 2007

(30) Foreign Application Priority Data

Nov. 1, 2005   (JP)  ............................. 2005-318912
Sep. 25, 2006  (JP)  ............................. 2006-258623

(51) Int. Cl.
   *A61B 3/10*   (2006.01)
(52) U.S. Cl. ........................ 351/212; 351/205
(58) Field of Classification Search ................ 351/212, 351/205, 211, 246, 247, 208, 200, 221; 600/403, 600/404, 405
   See application file for complete search history.

(56) References Cited

U.S. PATENT DOCUMENTS

| | | | |
|---|---|---|---|
| 4,991,584 A | | 2/1991 | Kobayashi et al. |
| 5,056,522 A | * | 10/1991 | Matsumura et al. ......... 600/405 |
| 5,131,739 A | | 7/1992 | Katsuragi |
| 5,463,430 A | | 10/1995 | Isogai et al. |
| 5,474,066 A | | 12/1995 | Grolman |
| 5,523,808 A | | 6/1996 | Kohayakawa |
| 5,565,939 A | | 10/1996 | Fujieda |
| 5,822,034 A | * | 10/1998 | Shimashita et al. ......... 351/212 |
| 6,022,108 A | | 2/2000 | Yoshida et al. |
| 2004/0189936 A1 | | 9/2004 | Mimura et al. |
| 2005/0157261 A1 | | 7/2005 | Hanebuchi et al. |

FOREIGN PATENT DOCUMENTS

| | | |
|---|---|---|
| EP | 0 310 045 A1 | 4/1989 |
| EP | 1 464 272 A1 | 10/2004 |
| JP | A 63-197433 | 8/1988 |
| JP | A 01-265937 | 10/1989 |
| JP | A 06-046999 | 2/1994 |
| JP | A 06-047003 | 2/1994 |
| JP | A 07-194557 | 1/1995 |
| JP | A 08-010222 | 1/1996 |
| JP | A 08-507463 | 8/1996 |
| JP | A 10-071122 | 3/1998 |
| JP | A 2004-313758 | 11/2004 |
| JP | A 2005-185523 | 7/2005 |

* cited by examiner

*Primary Examiner*—Hung X. Dang
(74) *Attorney, Agent, or Firm*—Oliff & Berridge, PLC (57) ABSTRACT

An ophthalmic apparatus with which it is easy to open eyelids of an examinee at the time of intraocular pressure measurement has a measurement unit including an measurement part measuring intraocular pressure by blowing fluid to a cornea of an examinee's eye via a nozzle to deform the cornea and a measurement part having a measurement optical system for measuring eye characteristics of the eye, wherein the intraocular pressure measurement part is placed above the eye characteristic measurement part, a device making a selective changeover between an intraocular pressure measurement mode and an eye characteristic measurement mode, and a first movement mechanism part moving the measurement unit in an up-and-down direction with respect to the eye so that a measurement optical axis of either of the measurement parts to be used for the selected mode is positioned at approximately the same height as the examinee's eye.

9 Claims, 7 Drawing Sheets

OPHTHALMIC APPARATUS

BACKGROUND OF THE INVENTION

1. Field of the Invention

The present invention relates to an ophthalmic apparatus for measuring (examining) intraocular pressure and eye characteristics such as eye refractive power.

2. Description of Related Art

Conventionally, there is a multifunction ophthalmic apparatus for measuring (examining) intraocular pressure and eye characteristics such as eye refractive power. Proposed as this kind of ophthalmic apparatus is one having a configuration that an eye characteristic measurement part which performs measurement (examination) of eye characteristics of an examinee's eye is placed above an intraocular pressure measurement part which performs noncontact measurement of intraocular pressure of the examinee's eye by blowing fluid to a cornea of the examinee's eye.

Incidentally, it is necessary to perform intraocular pressure measurement with eyelids of an examinee widely open; accordingly, in the case of intraocular pressure measurement with the apparatus as mentioned above, it is often the case that an examiner reaches out his/her hand to open the eyelids of the examinee. However, in the case of the apparatus as mentioned above, it is difficult to open the eyelids of the examinee since a working distance between the examinee's eye and a front end of the apparatus is short and the eye characteristic measurement part is placed above the intraocular pressure measurement part.

SUMMARY OF THE INVENTION

An object of the invention is to overcome the problems described above and to provide an ophthalmic apparatus with which it is easy to open eyelids of an examinee at the time of intraocular pressure measurement.

To achieve the objects and in accordance with the purpose of the present invention, an ophthalmic apparatus has a measurement unit including an intraocular pressure measurement part which measures intraocular pressure by blowing fluid to a cornea of an examinee's eye via a nozzle to deform the cornea, and an eye characteristic measurement part which has a measurement optical system for measuring eye characteristics of the examinee's eye, wherein the intraocular pressure measurement part is placed above the eye characteristic measurement part, measurement mode changeover means which makes a selective changeover between an intraocular pressure measurement mode and an eye characteristic measurement mode, and a first movement mechanism part which moves the measurement unit in an up-and-down direction with respect to the examinee's eye so that a measurement optical axis of either of the intraocular pressure measurement part and the eye characteristic measurement part to be used for the selected measurement mode is positioned at approximately the same height as the examinee's eye.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1A:
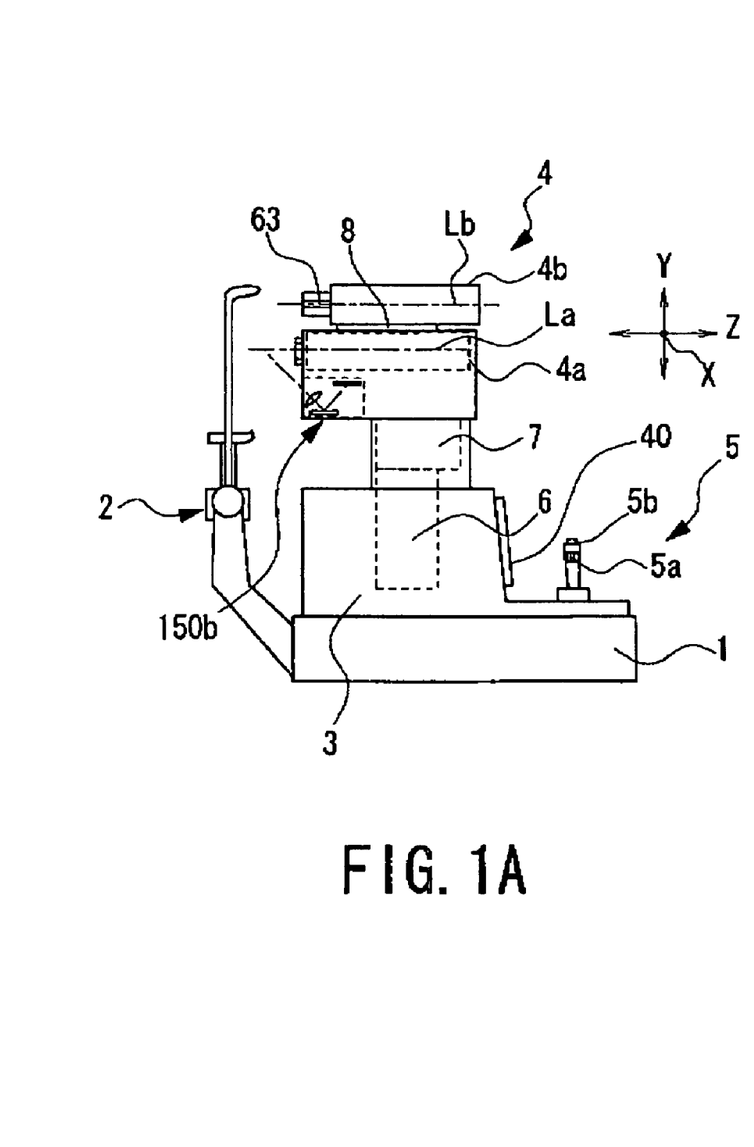
FIGS. 1A and 1B are schematic external views showing an ophthalmic apparatus consistent with one preferred embodiment of the present invention.
Figure 1B:
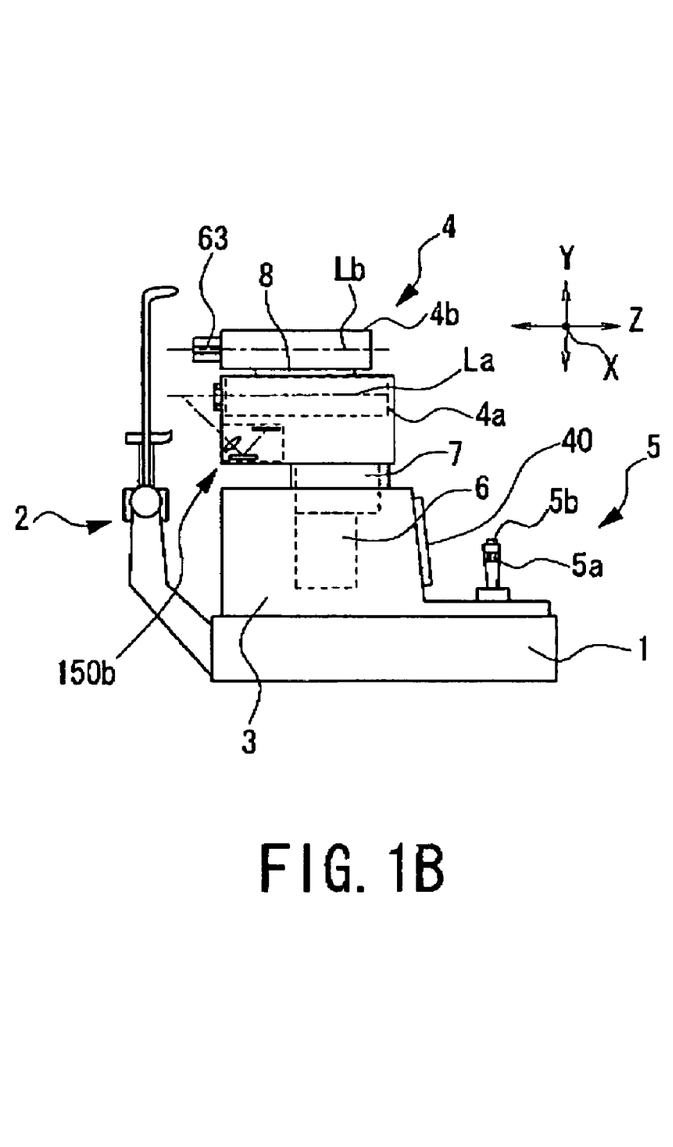

A detailed description of one preferred embodiment of an ophthalmic apparatus embodied by the present invention is provided below with reference to the accompanying drawings. In this embodiment, a multifunctional ophthalmic apparatus for measuring eye refractive power, a corneal shape, corneal thickness and intraocular pressure will be described as an example. FIGS. 1A and 1B are views showing a schematic configuration of the ophthalmic apparatus consistent with the preferred embodiment of the present invention. FIG. 1A shows a state of the apparatus at the time of measurement of the eye refractive power, the corneal shape and the corneal thickness, and FIG. 1B shows a state of the apparatus at the time of measurement of the intraocular pressure.

The ophthalmic apparatus includes a base 1, a face (head) supporting unit 2 attached to the base 1, a mobile base 3 provided movably on the base 1, and a measurement unit 4 provided movably on the mobile base 3. The measurement unit 4 includes an eye characteristic measurement part 4a for performing measurement of the eye refractive power and the corneal shape of an examinee's eye E and an intraocular pressure measurement part 4b, arranged above the eye characteristic measurement part 4a, for performing noncontact measurement of the intraocular pressure. In other words, in the measurement unit 4, the eye characteristic measurement part 4a and the intraocular pressure measurement part 4b are placed so that a measurement optical axis Lb of the intraocular pressure measurement part 4b is positioned higher than a measurement optical axis La of the eye characteristic measurement part 4a.

By a Y-movement mechanism part 6 provided on the mobile base 3, the measurement unit 4 is moved in an up-and-down direction (a Y-direction in FIGS. 1A and 1B) with respect to the eye E of the examinee fixed by the face supporting unit 2. Specifically, by the Y-movement mechanism part 6, the measurement unit 4 is moved so that the optical axis La of the eye characteristic measurement part 4a is positioned at approximately the same height as the eye E in response to a changeover to an eye characteristic measurement mode, or so that the optical axis Lb of the intraocular pressure measurement part 4b is positioned at approximately the same height as the eye E in response to a changeover to an intraocular pressure measurement mode. For this purpose, it is necessary to keep a travel amount (driving amount) of the Y-movement mechanism part 6 greater than a distance between the optical axis La and the optical axis Lb, and it is preferable to keep it to such an extent that automatic alignment of the eye characteristic measurement part 4a or the intraocular pressure measurement part 4b with respect to the eye E in each of the measurement modes is performed smoothly.

In addition, by an XZ-movement mechanism part 7 provided on the Y-movement mechanism part 6, the measurement unit 4 is moved in a right-and-left direction (an X-direction in FIGS. 1A and 1B) and a back-and-forth direction (a direction of the working distance: a Z-direction in FIGS. 1A and 1B) with respect to the eye E of the examinee fixed by the face supporting unit 2. Accordingly, the measurement unit 4 is movable in a three-dimensional direction of the X-, Y-and Z-directions. Incidentally, the Y-movement mechanism part 6 and the XZ-movement mechanism part 7 are configured, for example, so that an X table movable in the X-direction is provided on a Y table movable in the Y-direction, a Z table movable in the Z-direction is provided on the X table, the measurement unit 4 is mounted on the Z table, and the tables are moved by respective motors and the like. For this kind of three-dimensional movement mechanism, a known configuration may be adopted and a detailed description is omitted.

In addition, by a Z-movement mechanism part 8, the intraocular pressure measurement part 4b is moved in the Z-direction with respect to the eye characteristic measurement part 4a. Specifically, by the Z-movement mechanism part 8, the intraocular pressure measurement part 4b is moved toward the eye E in response to the changeover to the intraocular pressure measurement mode or is moved away from the eye E in response to the changeover to the eye characteristic measurement mode.

By tilting operation of a joystick 5, the mobile base 3 is slid in the X-direction and the Z-direction on the base 1. In addition, by rotating operation of a rotation knob 5a, the measurement unit 4 is moved in the Y-direction by the Y-movement mechanism part 6. At the tip of the joystick 5, a measurement starting switch 5b is provided. In addition, a monitor 40 is provided on the mobile base 3.

Figure 2:
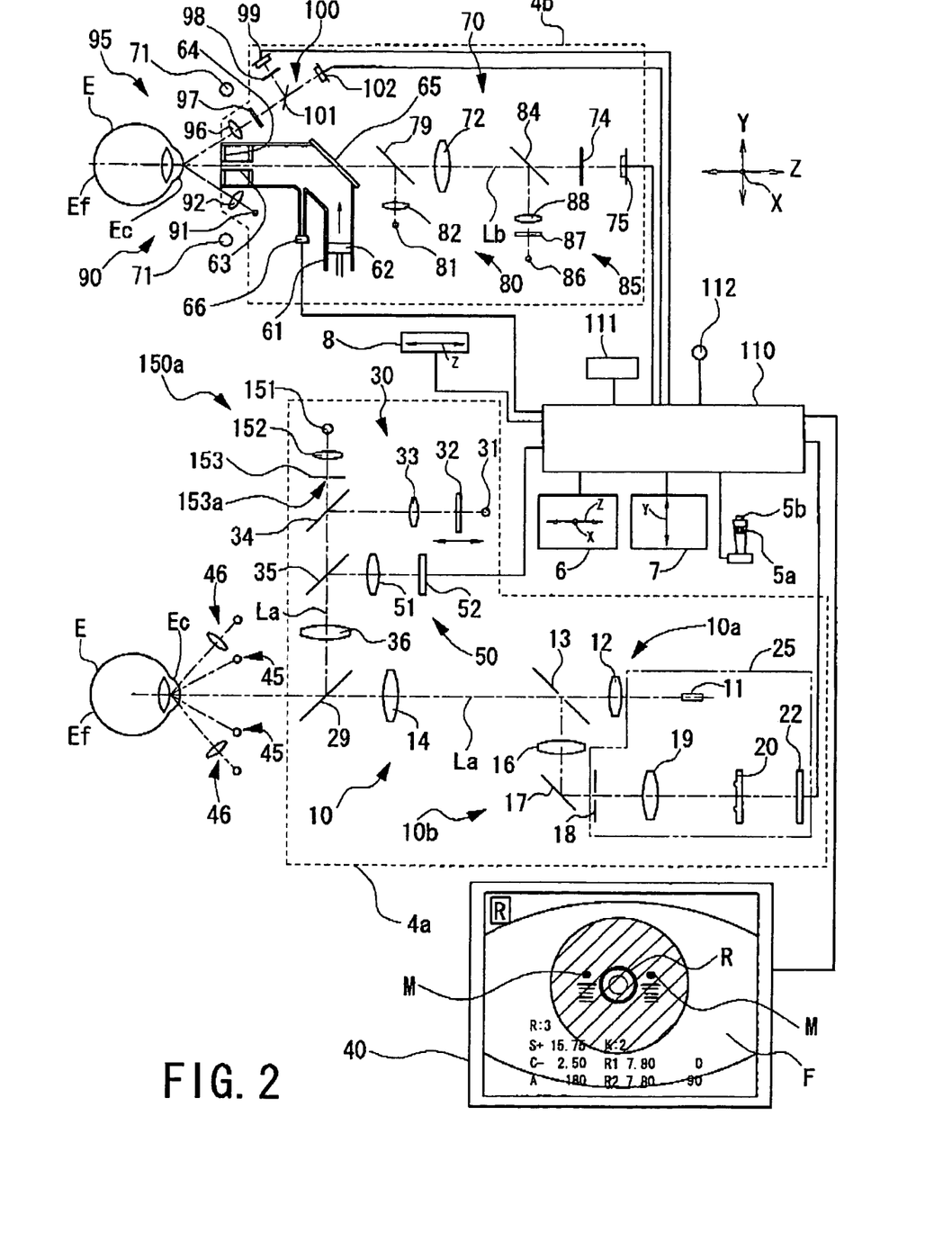
FIG. 2 is a view showing a schematic configuration of optical systems, a control system and the like of an eye characteristic measurement part and an intraocular pressure measurement part of the present ophthalmic apparatus.

FIG. 2 is a view showing a schematic configuration of optical systems, a control system and the like of the eye characteristic measurement part 4a and the intraocular pressure measurement part 4b of the present ophthalmic apparatus.

Initially, the optical system of the eye characteristic measurement part 4a will be described. An eye refractive power measurement optical system 10 for measuring the eye refractive power of the eye E includes a projection optical system 10a for projecting a measurement target (measurement light) in a spot shape onto a fundus Ef of the eye E via a central pupillary portion of the eye E, and an image-pickup (photo-receiving) optical system 10b for picking up fundus reflection light in a ring shape via a peripheral pupillary portion of the eye E and picking up a fundus reflection image in a ring shape by a two-dimensional image-pickup element.

The projection optical system 10a includes an infrared light source 11, a relay lens 12, a hole mirror 13 and an objective lens 14 for measurement, which are placed on the optical axis La of the measurement optical system 10. The light source 11 is placed in a position optically conjugate with the fundus Ef of the eye E with emmetropia. In addition, an opening of the hole mirror 13 is placed in a position optically conjugate with a pupil of the eye E.

Figure 4A:
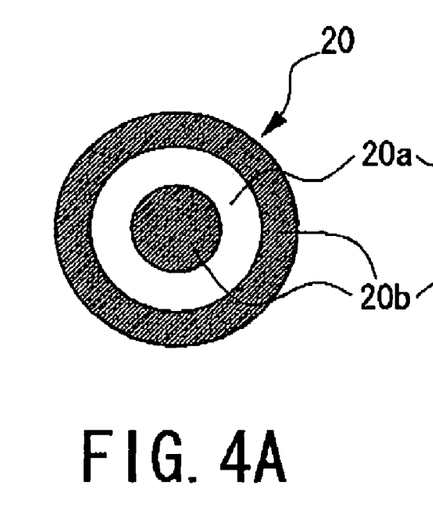
FIGS. 4A and 4B are views showing a schematic configuration of a ring lens.
Figure 4B:
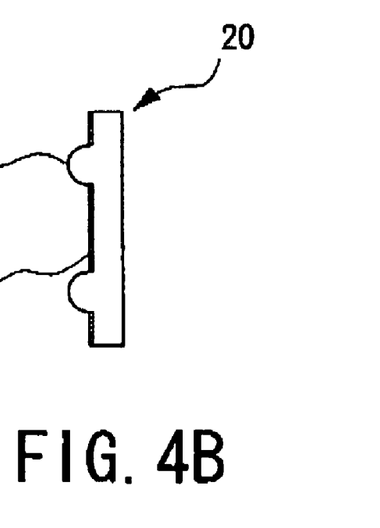

The image-pickup optical system 10b shares the objective lens 14 and the hole mirror 13 with the projection optical system 10a, and includes a relay lens 16 and a total reflection mirror 17 which are placed on the optical axis La in a reflecting direction of the hole mirror 13, and a photo-receiving diaphragm 18, a collimator lens 19, a ring lens 20 and a two-dimensional image-pickup element 22 which are placed on the optical axis La in a reflecting direction of the total reflection mirror 17. The photo-receiving diaphragm 18 and the image-pickup element 22 are placed in positions optically conjugate with the fundus Ef. As shown in FIGS. 4A and 4B, the ring lens 20 is constituted of a lens portion 20a where a cylindrical lens in a ring shape is formed on one side of a transparent plate, and a light shielding portion 20b formed of coating for light shielding which is provided to portions other than the ring-shaped cylindrical lens on the lens portion 20a, and is placed in a position optically conjugate with the pupil. Output from the image-pickup element 22 is inputted to a calculation and control part 110.

Incidentally, the eye refractive power measurement optical system is not limited to the one mentioned above, and known ones may be employed, for example, one which projects a measurement target (measurement light) in a ring shape onto the fundus Ef via the peripheral pupillary portion, picks up fundus reflection light via the central pupillary portion, and picks up a fundus reflection image in a ring shape by a two-dimensional image-pickup element.

A fixation target presenting optical system 30 includes a visible light source 31, a fixation target plate 32, a projection lens 33, a half mirror 34, a dichroic mirror 35 transmitting visible light and reflecting infrared light, and an objective lens 36 for observation, which are placed on the optical axis La in a reflecting direction of a half mirror 29 placed on the optical axis La. The light source 31 is placed in a position optically conjugate with the fundus Ef. The light source 31 and the fixation target plate 32 are movable in a direction of the optical axis La in order to perform fogging on the eye E.

In front of the half mirror 29, ring target projection optical systems 45, having infrared light sources, for projecting a ring target onto a cornea Ec of the eye E, and alignment target projection optical systems 46, having infrared light sources and collimator lenses, for projecting onto the cornea Ec infinite alignment targets for detecting an alignment state in the Z-direction of the eye characteristic measurement part 4a with respect to the eye E are placed symmetrically about the optical axis La. Incidentally, the ring target projection optical systems 45 double as an optical system for projecting a measurement target (measurement light) for measuring the corneal shape of the eye E, an optical system for projecting an alignment target for detecting an alignment state in the X-,Y-and Z-directions of the eye characteristic measurement part 4a with respect to the eye E, and an optical system for illuminating an anterior segment of the eye E.

An observation optical system 50 shares the half mirror 29, the objective lens 36 and the dichroic mirror 35 with the fixation target projection optical system 30, and includes an image-pickup lens 51 and a two-dimensional image-pickup element 52 which are placed on the optical axis La in a reflecting direction of the dichroic mirror 35. Output from the image-pickup element 52 is inputted to the calculation and control part 110. Accordingly, an image of the anterior segment of the eye E is picked up by the image-pickup element 52 to be displayed on the monitor 40. Incidentally, the observation optical system 50 doubles as an optical system for detecting an image of the ring target and images of the infinite alignment targets.

A projection optical system 150a for measuring the corneal thickness of the eye E shares the half mirror 34, the dichroic mirror 35, the objective lens 36 and the half mirror 29 with the fixation target presenting optical system 30, and includes a visible light source 151, a collective lens 152 and a slit plate 153 which are placed on the optical axis La in a transmitting direction of the half mirror 34. The slit plate 153 has a slit 153a of which a longitudinal direction corresponds to the X-direction, and is placed in a position optically conjugate with the cornea Ec.

Figure 3:
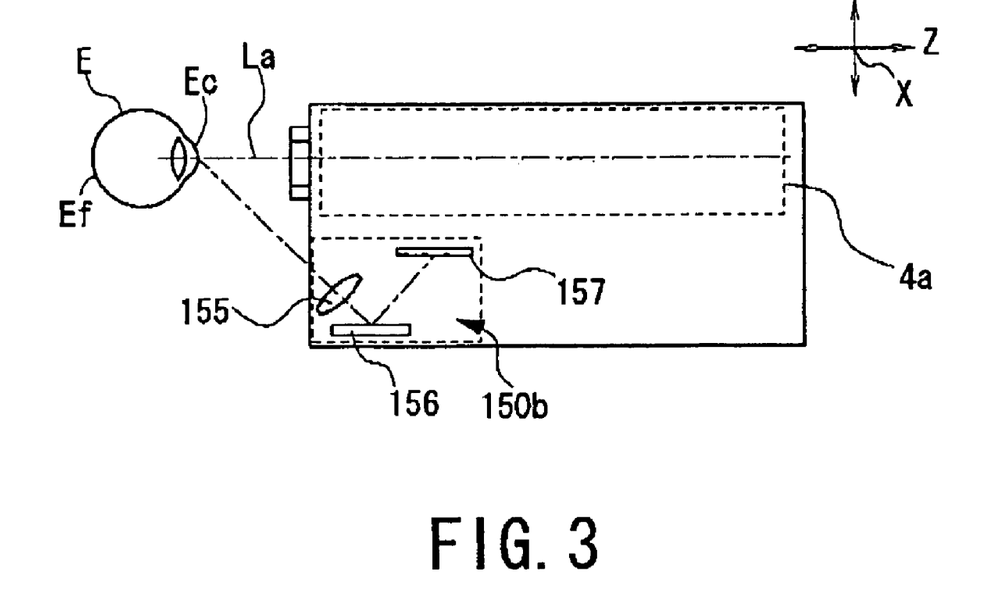
FIG. 3 is a view showing a schematic configuration of an image-pickup optical system for corneal thickness measurement.

An image-pickup (photo-receiving) optical system 150b for measuring the corneal thickness of the eye E is placed below the eye characteristic measurement part 4a as shown in FIGS. 1A, 1B and 3. The image-pickup optical system 150b includes an image-pickup lens 155, a total reflection mirror 156 and a two-dimensional image-pickup element 157, and picks up an image of a projected cross-section by the slit 153a based on the Scheimpflug's principle (for details, see Japanese Patent Application Unexamined Publication No. Sho63-197433).

Next, an air (fluid) blowing mechanism part of the intraocular pressure measurement part 4b is described (a detailed description will be given later). The air, which is compressed inside a cylinder (air compression chamber) 61 through movement of a piston 62 by driving force of a rotary solenoid 68 (see FIG. 9), is blown to the cornea Ec via a nozzle 63. The nozzle 63 is held by transparent glass plates 64. Behind the nozzle 63, a transparent glass plate 65 is placed, and behind the glass plate 65, the optical system described below is placed. Pressure inside the cylinder 61 is detected by a pressure sensor 66, and a signal from the pressure sensor 66 is inputted to the calculation and control part 110.

Next, the optical system of the intraocular pressure measurement part 4b is described. Incidentally, in the case of using the intraocular pressure measurement part 4b (at the time of intraocular pressure measurement), the intraocular pressure measurement part 4b is put to use with the end of the nozzle 63 of the intraocular pressure measurement part 4b projected toward the eye E relative to the front of a housing of the eye characteristic measurement part 4a.

Four infrared light sources 71 for illuminating the anterior segment of the eye E are placed having the optical axis Lb, which coincides with an axial line of the nozzle 63, at their center. An observation optical system 70 includes an objective lens 72 for observation, a filter 74 and a two-dimensional image-pickup element 75 which are arranged on the optical axis Lb. The filter 74 has a property of transmitting light from the light sources 71 and light from a light source 81 described later, and not transmitting light from a light source 91 described later. Output from the image-pickup element 75 is inputted to the calculation and control part 110. Accordingly, an image of the anterior segment of the eye E is picked up by the image-pickup element 75 to be displayed on the monitor 40. Incidentally, the observation optical system 70 doubles as an optical system for detecting an image of an alignment target for detecting an alignment state in the X-and Y-directions of the intraocular pressure measurement part 4b with respect to the eye E.

An alignment target projecting optical system 80 for projecting onto the cornea Ec the alignment target for detecting the alignment state in the X-and Y-directions of the intraocular pressure measurement part 4b with respect to the eye E includes the infrared light source 81 and a projection lens 82, which are arranged on the optical axis Lb in a reflecting direction of a half mirror 79 placed on the optical axis Lb. The light from the light source 81 is projected onto the cornea Ec from a front direction, and a corneal reflection image by the light source 81 is picked up by the image-pickup element 75. A signal from the image-pickup element 75 is inputted to the calculation and control part 110 to be utilized for the detection of the alignment state in the X-and Y-directions of the intraocular pressure measurement part 4b. Incidentally, a corneal reflection image by the light sources 71 may be utilized for the detection of the alignment state in the X-and Y-directions of the intraocular pressure measurement part 4b (for details, see U.S. Pat. No. 6,022,108 corresponding to Japanese Patent Application Unexamined Publication No. Hei10-71122).

A fixation target presenting optical system 85 includes a visible light source 86, a fixation target plate 87, and a projection lens 88, which are placed on the optical axis Lb in a reflecting direction of a dichroic mirror 84 placed on the optical axis Lb which transmits infrared light and reflects visible light.

A projection optical system 90 for detecting a deformation state of the cornea Ec includes the infrared light source 91 and a collimator lens 92. Incidentally, the projection optical system 90 doubles as an optical system for projecting an alignment target for detecting an alignment state in the Z-direction of the intraocular pressure measurement part 4b with respect to the eye E.

A photo-receiving optical system 95 for detecting the deformation state of the cornea Ec includes a photo-receiving lens 96, a filter 97, a pinhole plate 98 and a photodetector 99. The light from the light source 91 is made approximately parallel light by the collimator lens 92 to be projected onto the cornea Ec from an oblique direction, and a corneal reflection image by the light source 91 is photo-received by the photodetector 99. The filter 97 has a property of transmitting the light from the light source 91 and not transmitting the light from the light sources 71 and the light from the light source 81. The projection optical system 90 and the photo-receiving optical system 95 are placed so that a photo-receiving amount of the photodetector 99 becomes maximum when the cornea Ec is in a predetermined deformation state (flat state) A signal from the photodetector 99 is inputted to the calculation and control part 110.

In addition, an optical system 100 for detecting an image of the alignment target for detecting the alignment state in the Z-direction of the intraocular pressure measurement part 4b with respect to the eye E shares the photo-receiving lens 96 and the filter 97 with the photo-receiving optical system 95, and includes a one-dimensional position detector 102 placed in a transmitting direction of a half mirror 101. The corneal reflection image by the light source 91 enters also the position detector 102. A signal from the position detector 102 is inputted to the calculation and control part 110 to be utilized for the detection of the alignment state in the Z-direction of the intraocular pressure measurement part 4b.

Incidentally, in FIG. 2, the projection optical system 90 and the photo-receiving optical system 95 are illustrated as if they are arranged in the up-and-down direction (Y-direction) for the sake of convenience; however, they are actually arranged in the right-and-left direction (X-direction).

Next, the control system of the present ophthalmic apparatus is described. The calculation and control part 110, which performs control of the entire apparatus, calculation of measurement values and the like, is connected with the light sources, the image-pickup elements and the like of the eye characteristic measurement part 4a, the light sources, the image-pickup elements, the photodetector, the position detector, the pressure sensor and the like of the intraocular pressure measurement part 4b, the image-pickup element 157, the rotation knob 5a, the measurement starting switch 5b, the Y-movement mechanism part 6, the XZ-movement mechanism part 7, the Z-movement mechanism part 8, the monitor 40, a memory ill which stores a measurement result and the like, a measurement mode selecting switch 112, and the like.

In the ophthalmic apparatus having the configuration as above, its operations are described. The present apparatus has a first measurement mode for measuring only the eye refractive power and the corneal shape (an eye-refractive-power and corneal-shape measurement mode), a second measurement mode for measuring only the intraocular pressure (the intraocular pressure measurement mode), and a third measurement mode for measuring the eye refractive power, the corneal shape, the corneal thickness and the intraocular pressure (the eye characteristic measurement mode plus the intraocular pressure measurement mode). In the third measurement mode, the eye refractive power, the corneal shape and the corneal thickness are firstly measured, and the intraocular pressure is subsequently measured. This is because there is a possibility that an influence of the blowing of the compression air and the like on the eye E remains if the intraocular pressure is firstly measured. Hereinbelow, the third measurement mode is described.

Figure 5A:
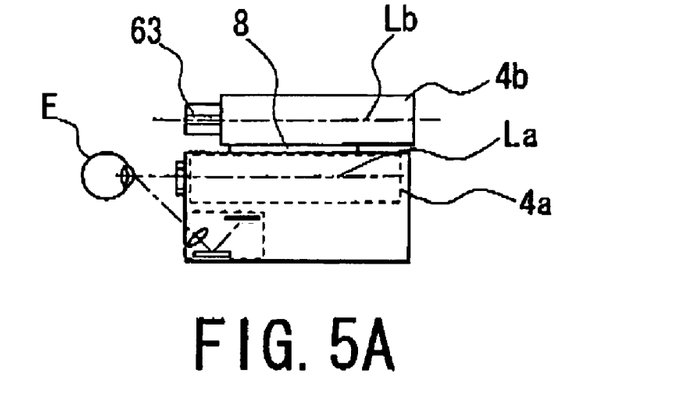
FIGS. 5A to 5C are views for illustrating movement of the eye characteristic measurement part and the intraocular pressure measurement part at the time of a changeover from an eye characteristic measurement mode to an intraocular pressure measurement mode.

When the third measurement mode is selected using the switch 112, the eye characteristic measurement mode is firstly implemented. In this case, the calculation and control part 110 initializes the height of the measurement unit 4 so that eye characteristic measurement is started smoothly. Specifically, the calculation and control part 110 drives the Y-movement mechanism part 6 to move the measurement unit 4 in the Y-direction so that the optical axis La of the eye characteristic measurement part 4a is positioned at approximately the same height as the eye E. In addition, the calculation and control part 110 drives the Z-movement mechanism part 8 to move the intraocular pressure measurement part 4b away from the eye E with respect to the eye characteristic measurement part 4a so that the end of the nozzle 63 is kept from contact with an examinee's face during the eye characteristic measurement. Thus, a state where the eye characteristic measurement can be carried out is achieved (see FIG. 5A).

Next, the alignment in the X-,Y-and Z-directions of the eye characteristic measurement part 4a with respect to the eye E is performed. As an anterior segment image F picked up by the image-pickup element 52 is displayed on the monitor 40 (see FIG. 2), an examiner performs rough alignment by operating the joystick 5 and the rotation knob 5a while observing the image F. When achieving a state where a ring target image R by the projection optical systems 45 and alignment target images M by the projection optical systems 46 can be picked up by the image-pickup element 52, the calculation and control part 110 drives the Y-movement mechanism part 6 and the XZ-movement mechanism part 7 to move the measurement unit 4 in the X-,Y-and Z-directions so that fine alignment of the eye characteristic measurement part 4a with respect to the eye E is performed. In this case, based on the central position of the detected ring target image R, the calculation and control part 110 obtains the alignment state in the X-and Y-directions of the eye characteristic measurement part 4 with respect to the eye E. In addition, based on a distance between the detected alignment target images M and a space in a predetermined meridional direction of the ring target image R, the calculation and control part 110 obtains the alignment state in the Z-direction of the eye characteristic measurement part 4a with respect to the eye E (for details, see U.S. Pat. No. 5,463,430 corresponding to Japanese Patent Application Unexamined Publication No. Hei6-46999).

In the case of an automatic measurement mode, measurement is automatically started upon completion of the alignment. On the other hand, in the case of a manual measurement mode, measurement is started when the alignment is completed and the examiner operates the switch. 5b.

The calculation and control part 110 firstly obtains the corneal shape of the eye E based on a shape of the ring target image R picked up by the image-pickup element 52. Then, when a predetermined number of (for example, three) measurement values of the corneal shape except measurement errors are obtained, a shift to eye refractive power measurement is made.

Measurement light emitted from the light source 11 is projected onto the fundus Ef and forms a point light source image in a spot shape on the fundus Ef. The light of the point light source image formed on the fundus Ef is reflected and scattered to exit the eye E, is converged by the objective lens 14, is converged again on an opening of the photo-receiving diaphragm 18, is made to be approximate parallel light by the collimator lens 19 (if the eye E is emmetropia), is picked up as ring-shaped light by the ring lens 20, and is picked up by (photo-received on) the image-pickup element 22 as a ring image.

In the eye refractive power measurement, preliminary measurement is firstly performed, and based on a result of the preliminary measurement, the light source 31 and the fixation target plate 32 are moved in the direction of the optical axis La to perform fogging on the eye E. Next, main measurement is performed on the eye E under fogging.

The output from the image-pickup element 22 is stored in the image memory 111 as image data. Thereafter, based on the ring image stored in the image memory 111, the calculation and control part 110 obtains positions in meridian directions of the ring image. Next, based on the obtained positions of the ring image, the calculation and control part 110 performs least square fitting of ellipses to obtain an ellipse. Then, the calculation and control part 110 obtains refractive errors in the meridian directions based on the shape of the obtained ellipse, and obtains the eye refractive power (sphere power, cylinder power and an astigmatic axial angle) of the eye E based on the refractive errors. Then, when a predetermined number of (for example, three) measurement values of the eye refractive power except measurement errors are obtained, a shift to corneal thickness measurement is made.

Measurement light emitted from the light source 151 is made to be slit light to be projected onto the cornea Ec. Then, a sectional image of the cornea Ec by the slit light is picked up by the image-pickup element 157.

Figure 6:
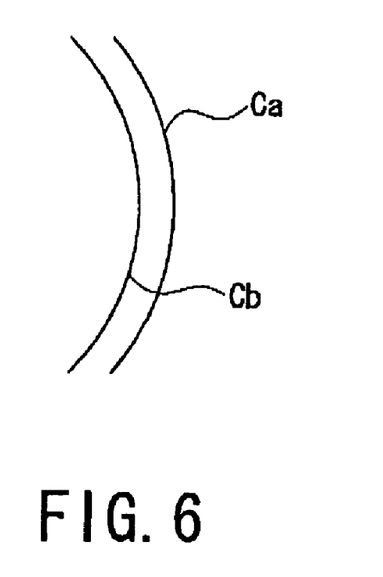
FIG. 6 is a view showing a corneal sectional image picked up by an image-pickup element for corneal thickness measurement.

FIG. 6 is a view showing a corneal sectional image picked up by the image-pickup element 157. In FIG. 6, a reference letter Ca indicates a corneal anterior surface and a reference letter Cb indicates a corneal posterior surface, and shown is a correction image in consideration of magnification change with respect to positions caused by the Scheimpflug's principle. Here, the calculation and control part 110 obtains the corneal thickness of the eye E through image processing. At this time, the corneal thickness may be obtained from the entire corneal sectional image (for example, corneal thicknesses are obtained at a plurality of positions and an average thereof is obtained), or a corneal thickness at a certain portion of the corneal sectional image maybe obtained (for example, a corneal thickness at a position passing through a corneal center is obtained).

Figure 5B:
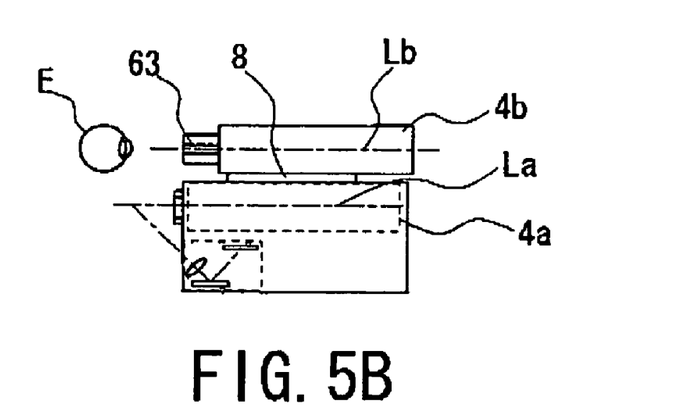

Then, when a predetermined number of (for example, three) measurement values of the corneal thickness except measurement errors are obtained, in the third measurement mode, the calculation and control part 110 automatically generates a signal for the changeover from the eye characteristic measurement mode to the intraocular pressure measurement mode. Then, the calculation and control part 110 drives the Y-movement mechanism part 6 to move the movement unit 4 downward so that the optical axis Lb of the intraocular pressure measurement part 4b is positioned at approximately the same height as the eye E (see FIG. 5B).

Figure 5C:
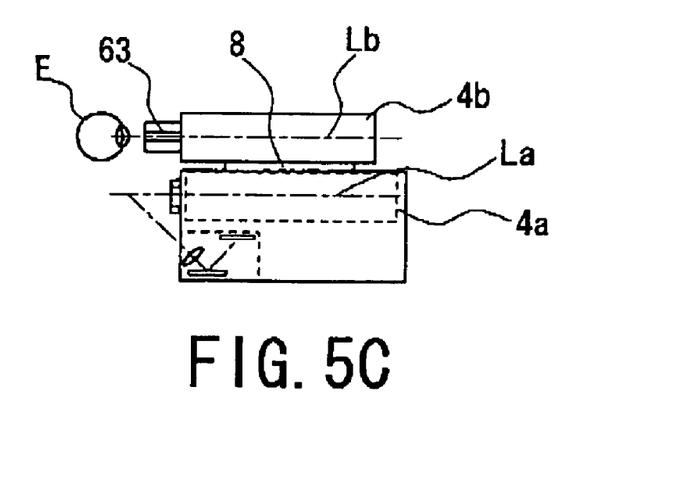

In addition, the calculation and control part 110 drives the Z-movement mechanism part 8 to move the intraocular pressure measurement part 4b toward the eye E so that the end of the nozzle 63 is projected toward the eye E (i.e., positioned on the eye E's side) relative to the front of the housing of the eye characteristic measurement part 4a. This is performed so that, when the intraocular pressure measurement is performed, the front of the housing of the eye characteristic measurement part 4a is kept from contact with the examinee's face and the working distance between the eye E and the apparatus is shortened to suit with the intraocular pressure measurement. Accordingly, a state where intraocular pressure measurement can be carried out is achieved (see FIG. 5C).

Incidentally, in the case of moving the intraocular pressure measurement part 4b toward the eye E, the end of the nozzle 63 may come into contact with the eye E; accordingly, it is preferable that the XZ-movement mechanism part 7 is driven to once move the measurement unit 4 to a reference position in a direction away from the eye E (for example, to move the measurement unit 4 to a reference position set on the rearmost side), and thereafter, the end of the nozzle 63 is projected by a predetermined amount.

When achieving a state where the corneal reflection image by the light source 91 can enter the position detector 102, the calculation and control part 110 drives the XZ-movement mechanism part 7 to move the measurement unit 4 in the Z-direction so as to perform fine alignment of the intraocular pressure measurement part 4b with respect to the eye E. In addition, in response to the changeover signal to the intraocular pressure measurement mode, the calculation and control part 110 controls to make a changeover of the image displayed on the monitor 40 from the anterior segment image by the image-pickup element 52 to the anterior segment image by the image-pickup element 75, and when achieving a state where the corneal reflection image by the light source 81 can be picked up by the image-pickup element 75, drives the Y-movement mechanism part 6 and the XZ-movement mechanism part 7 to move the measurement unit 4 in the X- and Y-directions so as to perform fine alignment of the intraocular pressure measurement part 4b with respect to the eye E.

When the alignment states in the X-, Y- and Z-directions of the intraocular pressure measurement part 4b with respect to the eye E fall within respective allowable ranges, the calculation and control part 110 automatically generates a trigger signal (or, in response to a display of alignment completion displayed on the monitor 40, the examiner pushes the switch 5b to input a trigger signal) to drive the rotary solenoid 68. When the piston 62 is moved by the driving of the rotary solenoid 68, the air inside the cylinder 61 is compressed, and the compressed air is blown from the nozzle 63 to the cornea Ec. The cornea Ec is gradually deformed by the blowing of the compressed air, and when brought to the flat state, the maximum amount of light enters the photodetector 99. The calculation and control part 110 obtains a value of the intraocular pressure based on a signal from the pressure sensor 66 and a signal from the photodetector 99.

When the intraocular pressure value is obtained, the calculation and control part 110 corrects the intraocular pressure value based on the corneal thickness value measured in the eye characteristic measurement mode (see for example U.S. Pat. No. 5,474,066 corresponding to Japanese Patent Application Unexamined Publication No. Hei8-507463). Then, when a predetermined number of (for example, three) measurement values of the intraocular pressure except measurement errors are obtained, the intraocular pressure measurement is terminated.

As the intraocular pressure measurement part 4b is placed above the eye characteristic measurement part 4a as mentioned above, when the measurement unit 4 is moved downward at the time of the intraocular pressure measurement, a space above the housing of the measurement unit 4 becomes unoccupied; therefore, the examiner can easily open the eyelids of the eye E (for example, it becomes easier for the examiner to put his/her hand between the eye E and the apparatus, or it becomes easier to see a state of the eye E). In addition, as the intraocular pressure measurement part 4b is moved in the Z-direction with respect to the eye characteristic measurement part 4a, the nozzle 63 is moved away from the examinee's face at the time of the eye characteristic measurement, so that measurement is performed while the end of the nozzle 63 is kept from contact with the examinee's face.

Incidentally, in the above description, it is configured that the entire intraocular pressure measurement part 4b is moved in the Z-direction with respect to the eye characteristic measurement part 4a; however, the present invention is not limited thereto. It is essential only that the position of the end of the nozzle 63 of the intraocular pressure measurement part 4b is changed in the Z-direction with respect to the eye characteristic measurement part 4a. For example, only the nozzle 63 may be inserted into and removed out of the housing of the intraocular pressure measurement part 4b.

Figure 7:
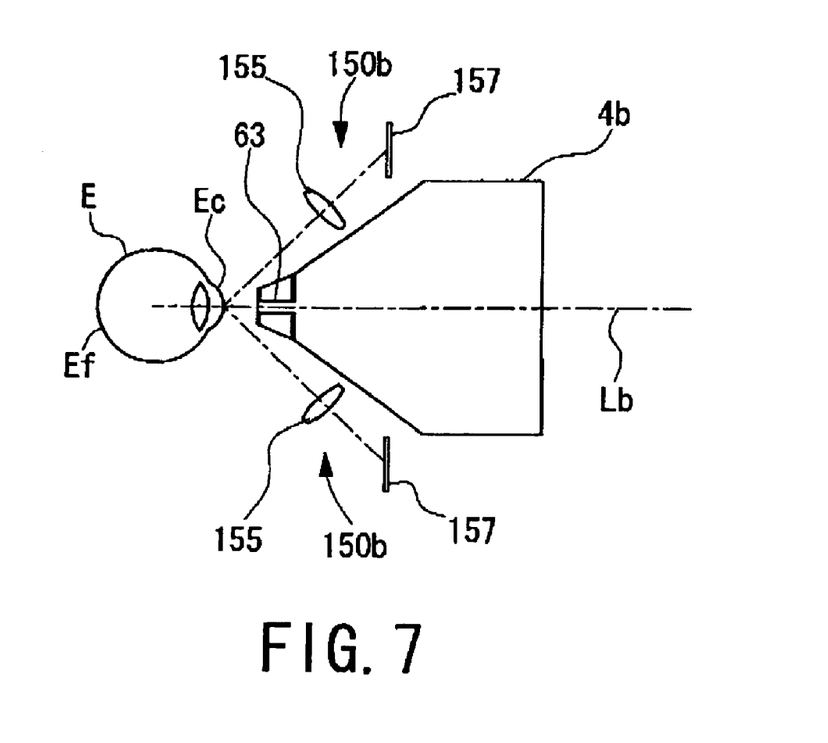
FIG. 7 is a view showing a schematic configuration of a modified embodiment of the image-pickup optical system for corneal thickness measurement.

In addition, in the above description, it is configured that the projection optical system 150a for corneal thickness measurement is provided inside the eye characteristic measurement part 4a and the image-pickup optical system 150b for corneal thickness measurement is provided below the eye characteristic measurement part 4a; however, it may be configured that the projection optical system 150a for corneal thickness measurement is provided inside the intraocular pressure measurement part 4b (for example, the projection optical system 150a for corneal thickness measurement is placed to have its optical axis coaxial with the optical axis of the fixation target presenting optical system 85 of the intraocular pressure measurement part 4b), and image-pickup optical systems 150b are provided on a right side and a left side of the intraocular pressure measurement part 4b (see FIG. 7). By such a configuration, when the second measurement mode for measuring only the intraocular pressure is selected, the corneal thickness for the correction of the intraocular pressure value can be measured without the use of the eye characteristic measurement part 4a. In addition, a projection optical system and an image-pickup optical system for corneal thickness measurement may be provided independent of the eye characteristic measurement part 4a and the intraocular pressure measurement part 4b.

Figure 8:
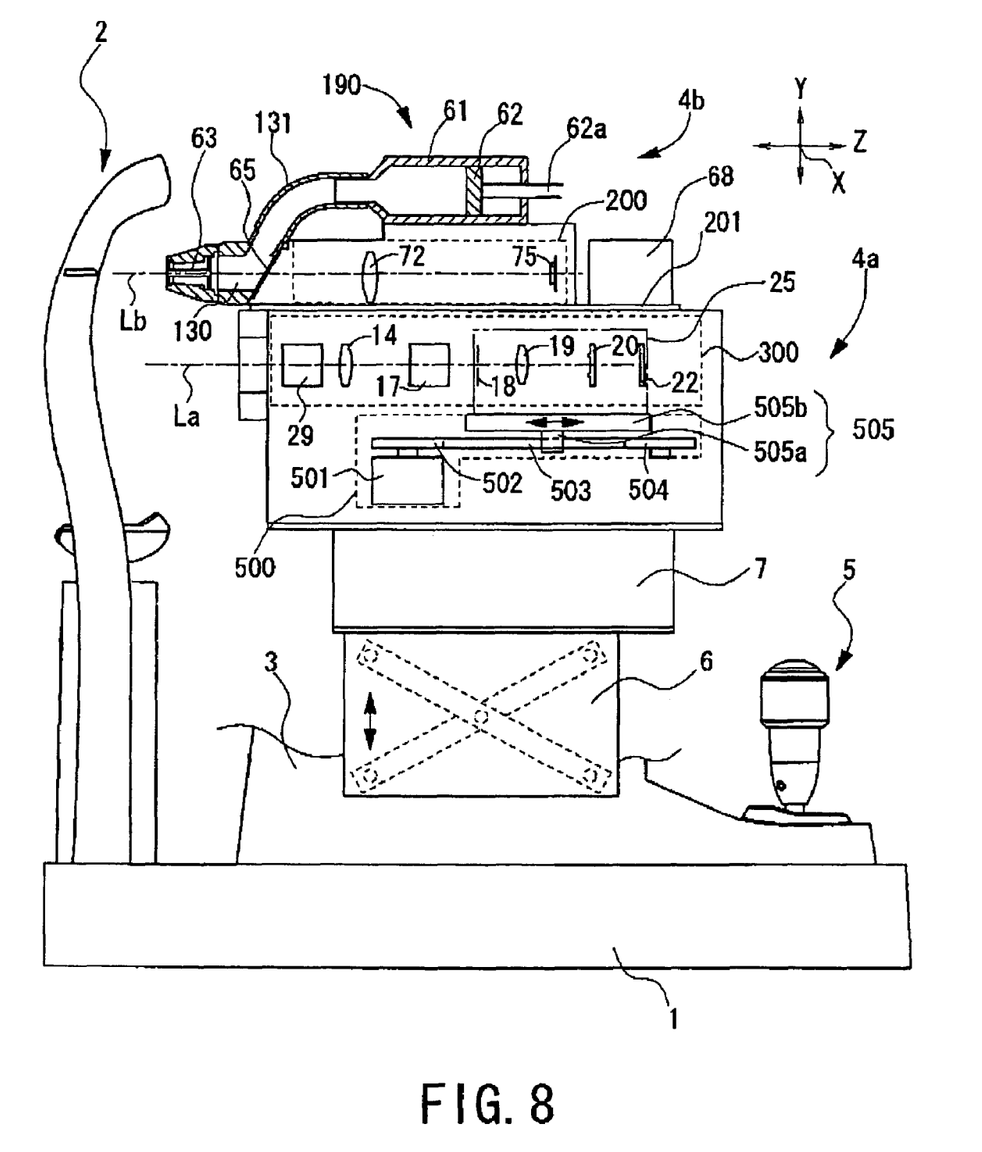
FIG. 8 is a view showing a schematic configuration of an air blowing mechanism part and movement mechanism parts of the present ophthalmic apparatus.
Figure 9:
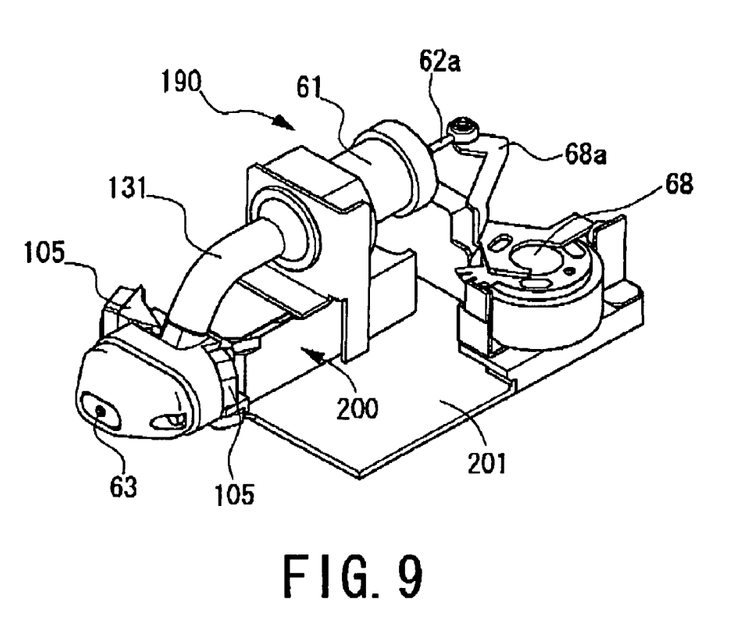
FIG. 9 is a perspective view showing the intraocular pressure measurement part.

FIG. 8 is a view showing a schematic configuration of the air blowing mechanism part and movement mechanism parts of the present ophthalmic apparatus. FIG. 9 is a perspective view of the intraocular pressure measurement part 4b.

First, the intraocular pressure measurement part 4b is described. An air blowing mechanism part 190 including the cylinder 61 and the piston 62 is placed above the optical axis Lb which coincides with the axial line of the nozzle 63. In addition, in a position approximately the same height as the optical axis Lb (or the nozzle 63), placed is an intraocular pressure measurement optical part 200 including the observation optical system 70, the projection optical system 80, the fixation target presenting optical system 85, and the like. In other words, the air blowing mechanism part 190 is placed above the intraocular pressure measurement optical part 200. In addition, below a stage 201 on which the intraocular pressure measurement optical part 200 and the like are mounted, the eye characteristic measurement part 4a is placed.

An arm 68a of the rotary solenoid 68 mounted on the state 201 is coupled to the piston 62 via a piston rod 62a. An airtight chamber 130 for enclosing the compressed air is coupled to the end of the cylinder 61 via a tube 131. The airtight chamber 130 is positioned at approximately the same height as the optical axis Lb, and the intraocular pressure measurement optical part 200 is placed behind the airtight chamber 130. In addition, an alignment optical part 105 including the projection optical system 90, the photo-receiving optical system 95 and the like is placed in the X-direction via the nozzle 63 and the airtight chamber 130.

When a trigger signal for starting the intraocular pressure measurement is inputted, the calculation and control part 110 drives the rotary solenoid 68 to rotate the arm 68a. Then, the piston 62 is moved forward by the rotation, so that the air compressed inside the cylinder 61 compresses the air inside the airtight chamber 130 via the tube 131. Accordingly, the compressed air is blown to the cornea Ec via the nozzle 63.

Next, the eye characteristic measurement part 4a is described. A movement mechanism part 500 for moving a movable optical part 25 constituted of a part of the optical members of the measurement optical system 10 (see FIGS. 2 and 8) is placed below the optical axis La. In addition, positioned at approximately the same height as the optical axis La is an eye characteristic measurement optical part 300 including the measurement optical system 10, the fixation target presenting optical system 30, the observation optical system 50 and the like. In other words, the movement mechanism part 500 is placed below the eye characteristic measurement optical part 300. Incidentally, the movable optical part 25 includes the light source 11, the photo-receiving diaphragm 18, the collimator lens 19, the ring lens 20, and the image-pickup element 22. In addition, the movable optical part 25 may include the fixation target 31 and the fixation target plate 32.

The movement mechanism part 500 includes a motor 501 connected to the calculation and control part 110, a pulley 502 attached to a rotation shaft of the motor 501, a belt 503 extending in the direction of the optical axis La, a pulley 504 provided behind the belt 503, a movement member 505 for moving the movable optical part 25. The pulley 502 is coupled to the pulley 504 via the belt 503. In addition, the belt 503 is fixed to a belt fixing part 505a of the movement member 505. In addition, a table part 505b of the movement member 505 is fixed to a bottom face of the movable optical part 25. When the pulley 502 is rotated by rotation of the motor 501, the movement member 505 is moved via the belt 503, so that the movable optical part 25 is moved in the direction of the optical axis La.

When a trigger signal for starting the eye refractive power measurement is inputted, the calculation and control part 110 performs preliminary measurement of the eye refractive power and, based on a result of the preliminary measurement, moves the light source 31 and the fixation target plate 32 to perform fogging on the eye E. In addition, the calculation and control part 110 drives the movement mechanism part 500 (motor 501) in accordance with a spherical refractive error (sphere power) of the eye E obtained in the preliminary measurement to move the movable optical part 25 in the direction of the optical axis La. Accordingly, the spherical refractive error of the eye E is corrected, and the light source 11, the photo-receiving diaphragm 18 and the image-pickup element 22 are adjusted to be in the positions optically conjugate with the fundus Ef. Then, when visibility of the eye E is corrected, main measurement is performed on the eye E under fogging. By doing so, a measurement range of the eye refractive power is enlarged and measurement accuracy is improved. Incidentally, in the above configuration, the motor 501, the pulley 502, the belt 503, the pulley 504 and the movement member 505 are placed below the eye characteristic measurement optical part 300; however, it may be configured that the motor 501 being a driving source is placed below the eye characteristic measurement optical part 300, and the movable optical part 25 is moved via a movement mechanism part placed above or alongside the eye characteristic measurement optical part 300.

Figure 10A:
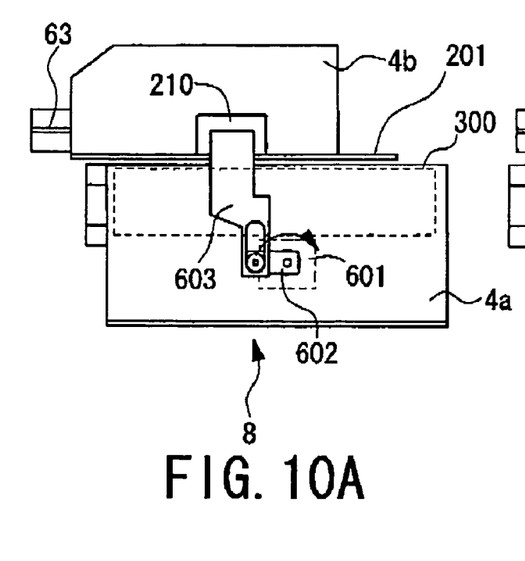
FIGS. 10A and 10B are views showing a schematic configuration of the movement mechanism part which moves the intraocular pressure measurement part in a back-and-forth direction with respect to the eye characteristic measurement part.
Figure 10B:
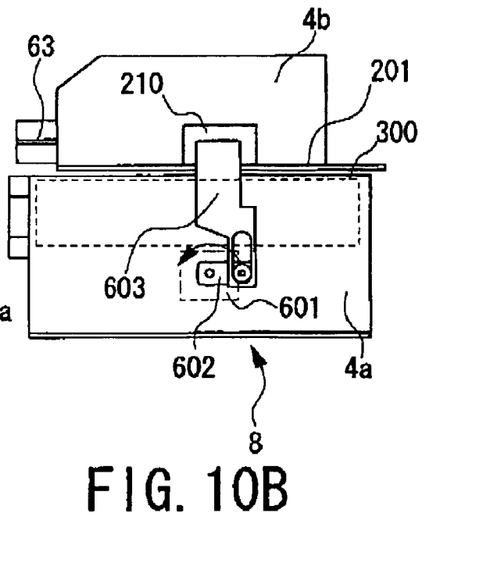

Next, the Z-movement mechanism part 8 which moves the intraocular pressure measurement part 4b in the Z-direction with respect to the eye characteristic measurement part 4a is described. FIG. 10A shows a state of the Z-movement mechanism part B at the time of the intraocular pressure measurement, and FIG. 10B shows a state of the Z-movement mechanism part 8 at the time of the eye characteristic measurement. The Z-movement mechanism part 8 has a motor 601 connected to the calculation and control part 110, and is placed below the eye characteristic measurement optical part 300. Specifically, the Z-movement mechanism part 8 is placed in a left side part of the eye characteristic measurement part 4a and closer to the left side than the movement mechanism part 500. In addition, a crank arm 602 is attached to the motor 601, and a coupling member 603 is coupled to the crank arm 602. In addition, the coupling member 603 placed on a side surface of the eye characteristic measurement optical part 300 is fixed to an attachment member 210 attached to the stage 201. In addition, the stage 201 is movable in the z-direction with respect to the eye characteristic measurement part 4a by an unillustrated guide mechanism. When the crank arm 602 is rotated by rotation of the motor 601, the attachment member 210 is moved via the coupling member 603, so that the intraocular pressure measurement part 4b is moved in the Z-direction. In other words, by driving the Z-movement mechanism part 8 placed below the optical axis La, the intraocular pressure measurement part 4b placed above the eye characteristic measurement optical part 300 is moved. Incidentally, for the guide mechanism, conceived is such a configuration that guide rods extending in the Z-direction are fixed to the right and left side surfaces of the eye characteristic measurement part 4a, and movement members inserted into and passing through the guide rods and moved in the Z-direction are fixed to the stage 201.

As mentioned above, in the measurement unit 4 in which the intraocular pressure measurement part 4b is placed above the eye characteristic measurement part 4a, the air blowing mechanism part 190 of the intraocular pressure measurement part 4b is placed above the intraocular pressure measurement optical part 200, and the movement mechanism part 500 of the eye characteristic measurement part 4a is placed below the eye characteristic measurement optical part 300; accordingly, a distance in the Y-direction between the optical axis La of the eye characteristic measurement part 4a and the optical axis Lb of the intraocular pressure measurement part 4b can be shortened. Thus, a travel distance in the Y-direction of the measurement unit 4 can be shortened, and a driving distance of the Y-movement mechanism part 6 can be shortened. In addition, it is possible to shorten a time for moving the optical axis La or the optical axis Lb to a predetermined height upon completion of the measurement of one of the eye characteristics in order to shift to the measurement of the other one of the eye characteristics.

Incidentally, it is also favorable to only make the placement of the air blowing mechanism part 190 of the intraocular pressure measurement part 4b above the intraocular pressure measurement optical part 200. The placement of the air blowing mechanism part 190 of the intraocular pressure measurement part 4b above the intraocular pressure measurement optical part 200 provides spaces in their side portions, so that an upper right part and an upper left part of the housing of the apparatus can be made small. Accordingly, the examiner can reach out his/her hand from the side portion of the apparatus to easily open the eyelids of the examinee. Incidentally, the air blowing mechanism part 190 may be placed alongside the intraocular pressure measurement optical part 200.

It is also favorable to only make the placement of the movement mechanism part 500 of the eye characteristic measurement part 4a below the eye characteristic measurement optical part 300. As the movement mechanism part 500 is not placed above the eye characteristic measurement optical part 300, a distance from the optical axis La of the eye characteristic measurement part 4a to the top face of the housing of the measurement unit 4 can be shortened, so that it becomes easy to open the eyelids at the time of the eye characteristic measurement. Incidentally, the movement mechanism part 500 may be placed alongside the eye characteristic measurement optical part 300.

In addition, as the Z-movement mechanism part 8 which moves the intraocular pressure measurement part 4b with respect to the eye characteristic measurement part 4a is placed below the optical axis La of the eye characteristic measurement part 4a, the distance between the optical axis La and the optical axis Lb can be shortened, and the intraocular pressure measurement part 4b can be miniaturized.

Incidentally, the movement mechanism part 500 is means for correcting the visibility of the examinee's eye in the above description but is not limited thereto For example, even if the movement mechanism part 500 is means for changing the position of the fixation target plate 32 in the direction of the optical axis La, the present invention is applicable, or the movement mechanism part 500 may act as both of the means for correcting the visibility of the examinee's eye and the means for changing the position of the fixation target plate 32 in the direction of the optical axis La.

In addition, an optical member for decentering the measurement light and a rotation mechanism part which rotates this optical member may be provided to the measurement optical system 10 (for details, see US 2005/157261 A1 corresponding to Japanese Patent Application Unexamined Publication No. 2005-185523).

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
a measurement unit including
an intraocular pressure measurement part which measures intraocular pressure by blowing fluid to a cornea of an examinee's eye via a nozzle to deform the cornea, and
an eye characteristic measurement part which has a measurement optical system for measuring eye characteristics of the examinee's eye,
wherein the intraocular pressure measurement part is placed above the eye characteristic measurement part;
measurement mode changeover means which makes a selective changeover between an intraocular pressure measurement mode and an eye characteristic measurement mode; and
a first movement mechanism part which moves the measurement unit in an up-and-down direction with respect to the examinee's eye so that a measurement optical axis of either of the intraocular pressure measurement part and the eye characteristic measurement part to be used for the selected measurement mode is positioned at approximately the same height as the examinee's eye.

2. The ophthalmic apparatus according to claim 1, further comprising a position changing mechanism part which changes a position of an end of the nozzle of the intraocular pressure measurement part in a back-and-forth direction with respect to the eye characteristic measurement part.

3. The ophthalmic apparatus according to claim 2, wherein the position changing mechanism part includes a second movement mechanism part which moves the intraocular pressure measurement part toward the examinee's eye when the intraocular pressure measurement mode is selected, and moves the intraocular pressure measurement part away from the examinee's eye when the eye characteristic measurement mode is selected.

4. The ophthalmic apparatus according to claim 1, wherein the eye characteristic measurement part has at least one of an eye refractive power measurement optical system for measuring eye refractive power of the examinee's eye and a corneal shape measurement optical system for measuring a corneal shape of the examinee's eye.

5. The ophthalmic apparatus according to claim 1, wherein one of the intraocular pressure measurement part and the eye characteristic measurement part has a corneal thickness measurement optical system for measuring corneal thickness of the examinee's eye.

6. The ophthalmic apparatus according to claim 1, wherein the intraocular pressure measurement part includes a fluid blowing mechanism part having a fluid compression chamber for compressing the fluid to be blown to the cornea, and the compression chamber is placed above or alongside the measurement optical axis of the intraocular pressure measurement part.

7. The ophthalmic apparatus according to claim 6, wherein the eye characteristic measurement part includes a third movement mechanism part which moves a part of optical members included in the measurement optical system for measuring the eye characteristics, and the third movement mechanism part is placed below or alongside the measurement optical axis of the eye characteristic measurement part.

8. The ophthalmic apparatus according to claim 7, wherein the third movement mechanism part is one of means which changes a position of a fixation target for fixating the examinee's eye in a direction of the optical axis by moving the part of the optical members, and means which corrects visibility of the examinee's eye by moving the part of the optical members.

9. The ophthalmic apparatus according to claim 6, further comprising a position changing mechanism part which changes a position of an end of the nozzle of the intraocular pressure measurement part in a back-and-forth direction relative to the eye characteristic measurement part, wherein the position changing mechanism part is placed below the measurement optical axis of the eye characteristic measurement part.

\* \* \* \* \*